United States Patent
Zhou et al.

(10) Patent No.: US 7,132,454 B2
(45) Date of Patent: Nov. 7, 2006

(54) HEXIM1 AS A SUPPRESSOR OF HIV REPLICATION AND CARDIAC HYPERTROPHY

(75) Inventors: Qiang Zhou, Berkeley, CA (US); Jasper H. N. Yik, Berkeley, CA (US); Ruichuan Chen, Berkeley, CA (US)

(73) Assignee: Regents of the University of California, Oakland, CA (US)

( * ) Notice: Subject to any disclaimer, the term of this patent is extended or adjusted under 35 U.S.C. 154(b) by 140 days.

(21) Appl. No.: 10/928,009

(22) Filed: Aug. 27, 2004

(65) Prior Publication Data

US 2006/0047004 A1     Mar. 2, 2006

(51) Int. Cl.
*A61K 31/16*     (2006.01)
*A61K 31/44*     (2006.01)

(52) U.S. Cl. ..................... 514/613; 514/340

(58) Field of Classification Search ............... 514/613, 514/340
See application file for complete search history.

(56) References Cited

U.S. PATENT DOCUMENTS

2003/0235588 A1*   12/2003   Richon et al. ............ 424/146.1

OTHER PUBLICATIONS

Yik et al. "Inhibition of P-TEFb (CDK9/Cyclin T) kinase and RNA polymerase II transcription by the Coordinated actions of HEXIM 1 and 7SK snRNA," Molecular Cells, Oct. 2003, vol. 12, pp. 971-982.*

Michels et al. "MAQ1 and 7SK RNA interact with CDK9/cyclin T complexes in A transcription-dependent Manner," Molecular and Cell Biology, Jul. 2003, vol. 23, No. 14, pp. 4859-4869.*

Ouchida et al. "Suppression of NF-kB-dependent gene expression by a hexamethylene bisacetamide-inducible protein HEXIM 1 inhuman vascular smooth muscle cell," Genes to Cell, Aug. 2003, pp. 95-107.*

Butler et al., Inhibition of Transformed Cell Growth and Induction of Cellular Differentiation by Pyroxamide . . . , Clin Cancer Res. 2001, 7:962-970.

Richon et al., A class of hybrid polar inducers of transformed cell differentiation inhibits histone deacetylases, Proc Natl Acad Sci U S A. (1998) 95:3003-3007.

Richon et al., Second generation hybrid polar compounds are potent inducers of transformed cell differentiation, Proc Natl Acad Sci U S A. (1996) 93:5705-5708.

Wang et al., New designed HMBA agents as Inducers of erythroleukemia cell differentiation, Chin Med Sci J. (2002) 17:27-31 (abstact only).

* cited by examiner

*Primary Examiner*—Shengjun Wang
(74) *Attorney, Agent, or Firm*—Richard Aron Osman

(57) ABSTRACT

Cellular transcription is modulated by increasing or decreasing the amount of active HEXIM1 in the cell. The methods are applied to the treatment of HIV infection and cardiac hypertrophy. Assays using reconstituted 7SK:P-TEFb snRNP screen for agents that modulate HEXIM1-P-TEFb binding.

6 Claims, No Drawings

HEXIM1 AS A SUPPRESSOR OF HIV REPLICATION AND CARDIAC HYPERTROPHY

This invention was made with Government support under Grants (Contracts) Nos. AI41757, GM64779 and NS43952, awarded by the National Institutes of Health. The Government has certain rights in this invention.

FIELD OF THE INVENTION

The field of the invention is HEXIM1 inhibition of human immunodeficiency virus (HIV) replication and cardiac hypertrophy.

BACKGROUND OF THE INVENTION

Hexamethylene bisacetamide (HMBA) induces cellular differentiation (e.g. Wang et al., Chin Med Sci J 2002, 17, 27–31), and has been shown to modulate the expression of a wide variety of genes (e.g. Zhang et al., August 2004, Int J Biochem Cell Biol, 36, 1613–23). It has also been reported to activate viruses, such as HSV (Yura et al., J Natl Cancer Inst 1991, 83, 186–9; McFarelane et al., J Gen Virol 1992, 73, 285–92) and HIV (e.g. Vlach et al., J Gen Virol. 1993, 74, 2401–8), and to inhibit human vascular smooth muscle cell (VSMC) proliferation (e.g. Ishikawa et al., Coron Artery Dis. 1997, 8, 28–32). Accordingly, HMBA and related compounds have been intensively studied as anti-cancer agents (e.g. Marks et al. C R Acad Sci III. 1999, February-March;322(2–3):161–5).

One HMBA-inducible protein of VSMCs, HEXIM1 (Kusuhara, et al. 1999, Biomed. Res. 20, 273–279), also known as HIS1, CLP1, MAQ1 and EDG1, has been reported to inhibit NFkB-activated transcription in VSMCs, and overexpressed HEXIM1 has been proposed as a strategy to therapeutically inhibit VSMC proliferation (Ouchida et al., Genes Cells (2003) 8:95–107). Independently, CLP-1 (cardiac lineage protein-1), the chicken and mouse ortholog of HEXIM1, has been suggested to play a role in cardiogenesis (Ghatpande et al., 1999, Dev Biol 208, 210–221; Ghatpande et al., 1999, Mol Cell Biochem. 96, 93–97; Huang et al., 2002, Gene 292, 245–259). Overexpression of CLP-1 inhibits the cardiac MLC-2v gene transcription (Huang et al., Mech Dev., 2004, 121:559–572; 2002). Also independently, increased expression of HEXIM1 has been reported to inhibit transcriptional activity in breast endothelial cells (Wittmann et al., Cancer Res. (2003) 63:5151–5158; Montano et al., U.S. Pat. No. 6,753,418; wherein HEXIM1 is referred to as EDG1). Also independently, Michels et al. (EMBO J., 2004, 23:2608–2619; and Mol Cell Biol., 2003, 23:4859–4869; wherein HEXIM1 is referred to as MAQ1) report that in HeLa cells, a HEXIM1-7SK RNA complex can bind CDK9/CyclinT (P-TEFb) as part of the 7SK snRNP.

P-TEFb serves not only as a general transcription factor but also a specific cellular cofactor for the HIV-1 Tat protein. Preventing Pol II from stalling is essential for HIV-1 transcription, during which P-TEFb is recruited to the nascent mRNA by Tat through formation of a ternary complex containing P-TEFb, Tat, and the HIV-1 TAR RNA, a stem-loop structure formed by the 5' end of the nascent viral transcript. Once recruited, P-TEFb phosphorylates the CTD and stimulates transcriptional elongation to produce the full-length HIV-1 transcripts.

Besides HIV-1 replication, the activation of P-TEFb also promotes cardiac hypertrophy, a disease characterized by the enlargement of cardiac myocytes. P-TEFb activity has been shown to be limiting for normal cardiac growth. Hypertrophic signals induce the release of 7SK and an increase in the cellular level of active, 7SK-free P-TEFb (Sano et al., Nat. Med., 2002, 8:1310–1317; Sano et al., Cell Cycle. 2003, 2, 99–104).

Practical utilization of HEXIM1 has been limited without any functional assignment for the protein. We disclose that P-TEFb is inhibited by HEXIM1 in a process that specifically requires 7SK for mediating the HEXIM1:P-TEFb interaction. We demonstrate that cellular transcription can be directly manipulated by increasing or decreasing HEXIM1 activity in the cell. More particularly, we show that HEXIM1 inhibits CDK9/Cyclin T, and can be used to inhibit cardiac hypertrophy and inhibit HIV replication. The disclosed methods for targeting fully differentiated cells, particularly non-proliferating cell types, such as hypertrophic cardiac myocytes provides unexpected therapeutic venues.

Relevant Literature

We have reported aspects of the present invention in Chen et al., J Biol Chem. 2004 Feb. 6;279(6):4153–60. Epub 2003 Nov. 19; Yik et al., Mol Cell Biol. (2004) 24:5094–105; and Yik et al., Mol Cell (2003) 12:971–982.

SUMMARY OF THE INVENTION

The invention provides methods and compositions for modulating cellular transcription by modulating the amount of HEXIM1 in target cells comprising 7SK RNA and P-TEFb.

In one embodiment, the invention provides methods for inhibiting HIV replication in a patient, the method comprising the steps of (a) determining that the patient is HIV-infected and a target for HEXIM1 therapy; (b) increasing the amount of active HEXIM1 in HIV-infected cells of the patient; and (e) detecting a resultant decrease in HIV replication at least 48 hr after the increasing step. The amount of HEXIM1 may be increased by introducing in the cell a viral vector that expresses recombinant HEXIM1, such as a lentiviral vector or a retroviral vector, wherein the HEXIM1 may be truncated at its N-terminus, such as 149 amino acid N-terminal truncation. Alternatively, the amount of HEXIM1 may be increased by introducing a hybrid polar HEXIM1 expression inducer, such as hexamethylene bisacetamide (HMBA), suberoylanilide hydroxamic acid (SAHA), m-carboxycinnamic acid bishydroxamide (CBHA), 6-(3-chlorophenylureido)caproic hydroxamic acid (3-Cl-UCHA), diethyl bis-(pentamethylene-N,N-dimethyl-carboxamide) malonate (EMBA), suberic bishydroxamic acid (SBHA), suberoyl-3-aminopyridincamide hydroxamic acid (pyroxamide), hexamethylene bis-(3-pyridin)amide (HMBPA), and ethylenediaminetetra acetic acid cobalt (Co-HDTA).

In another embodiment, the invention provides methods for inhibiting cardiac hypertrophy in a patient, the method comprising the steps of (a) determining that the patient has, or is susceptible to, cardiac hypertrophy, and is a target for HEXIM1 therapy; (b) increasing the amount of active HEXIM1 in cardiomyocytes of the patient; and (c) detecting a resultant inhibition in cardiac hypertrophy at least 48 hr after the increasing step. The amount of HEXIM1 may be increased by introducing in the cell a viral vector that expresses recombinant HEXIM1, such as a lentiviral vector or a retroviral vector, wherein the HEXIM1 may be truncated at its N-terminus, such as 149 amino acid N-terminal truncation. Alternatively, the amount of HEXIM1 may be increased by introducing a hybrid polar HEXIM1 expression inducer, such as hexamethylene bisacetamide (HMBA), suberoylanilide hydroxamic acid (SAHA), m-carboxycinnamic acid bishydroxamide (CBHA), 6-(3-chlorophenylureido)caproic hydroxamic acid (3-Cl-UCHA), diethyl bis-(pentamethylene-N,N-dimethylcarboxamide) malonate (EMBA), suberic bishydroxamic acid (SBHA), suberoyl-3-aminopyridineamide hydroxamic acid (pyroxamide), hexamethylene bis-(3-pyridin)amide (HMBPA), and ethylenediaminetetra acetic acid cobalt (Co-HDTA).

In another aspect, the invention provides a method of screening for an agent that modulates HEXIM1-P-TEFb binding, the method comprising the steps of (a) incubating a mixture of reconstituted 7SK RNA, P-TEFb, and HEXIM1, with a candidate modulating agent under conditions wherein but for the presence of the agent, the 7SK RNA, P-TEFb, and HEXIM1 engage in a reference binding; and (b) detecting an agent-biased binding of the HEXIM1 to the P-TEFb, wherein a difference between the reference binding and the agent-biased binding indicates that the agent modulates HEXIM1-P-TEFb binding. Binding may be detected in a kinase assay, an in vitro transcription assay, etc.

In yet another aspect, the invention provides a method of screening for an agent that inhibits pathogenesis associated with HEXIM1 underexpression, the method comprising the steps of (a) contacting pathogenically HEXIM1 underexpressing cell with an HEXIM1 upregulator, and (b) detecting a resultant inhibition of the pathogenesis, wherein the inhibition is selected from inhibition of HIV replication in an HIV-infected cell, and inhibition of hypertrophy in a cardiomyocyte that is hypertrophic or susceptible to hypertrophy, wherein the pathogenesis is HIV replication or cardiac hypertrophy.

DETAILED DESCRIPTION OF THE SPECIFIC EMBODIMENTS OF THE INVENTION

We demonstrate that cellular transcription can be directly manipulated by increasing or decreasing HEXIM1 activity in the cell. In particular applications, we show that increasing HEXIM1 activity inhibits pathogenic transcription associated with HIV infection and cardiac hypertrophy. One particular aspect of the invention is a method for modulating HIV transcription or replication, the method comprising the steps of (a) determining that a patient is HIV-infected and a target for HEXIM1 therapy; (b) increasing the amount of active HEXIM1 in HIV-infected cells of the patient; and (c) detecting a resultant decrease in HIV replication at least 48 hr after the increasing step.

Conventional diagnostic methods may be used to ascertain HIV infection. The primary tests for the diagnosis and confirmation of HIV infection are enzyme-linked immunosorbent assay (ELISA) and the Western blot. The ELISA, an inexpensive screening test for antibodies to HIV-1, is both sensitive and specific. The HIV-1 Western blot is a reliable confirmatory test following a repeatedly reactive ELISA. Rapid, point-of-care tests are also available, such as the FDA-approved OraQuick® (Abbott Laboratories) which uses finger-stick whole blood samples and can detect antibodies to HIV-1 within approximately 20 minutes. HIV-infected patients are generally determined to be targets or candidates for HEXIM1 therapy by confirming that the proposed HEXIM1 therapy is not contraindicated in the patient; for example, the patient does not present evidence of particular intolerance to the selected viral vector or HEXIM1 expression inducer.

In one embodiment, the HEXIM1 amount is increased by delivering to the cell exogenously produced HEXIM1 protein. A variety of methods exist for introducing exogenously produced proteins into cells are known in the art, and include protein transduction or protein therapy as described in publications by Nagahara et al. (e.g. Nagahara, et al., 1998, Nat Med. 4: 1449–52) and in publications from the laboratory of Dowdy (e.g. Nagahara, et al., 1998, Nat Med. 4: 1449–52.; Schwarze, et al., 1999, Science, 285:1569–72.; Vocero-Akbani, et al., 2000, Methods Enzymol, 322:508–21; Ho, et al., 2001, Cancer Res, 61:474–7.; Vocero-Akbani, et al., 2001, Methods Enzymol, 332:36–49; Snyder and Dowdy, 2001, Curr Opin Mol Ther, 3:147–52.; Becker-Hapak, et al., 2001, Methods, 24:247–56).

In a particular embodiment an eleven amino acid protein transduction domain (PTD), from the human immunodeficiency virus TAT protein (Green and Loewenstein, 1988, Cell, 55:1179–88; Frankel and Pabo, 1988, Cell, 55:1189–93) is fused to HEXIM1. The resulting HEXIM1-PTD fusion gene is incorporated into a plasmid or viral vector that facilitates introduction of the fusion gene into a convenient expression system such as E. coli. Purified fusion protein may be administered by a variety of methods, such as injection (e.g., intravenously) or aerosol inhalation.

In another embodiment, the HEXIM1 amount is increased by delivering to the cell a HEXIM1-expressing polynucleotide. Methods for delivering isolated polynucleotides to cells, including the nucleus of cells, are known, e.g. Fisher et al. (2000) Gene. Ther. 7: 1337–1343. In addition, HEXIM1 expression constructs may be entrapped in lipofectamine-DNA complexes, or in liposomes (e.g. Ghosh and Bachhawat, 1991, Targeted Diagn. Ther 4: 87–103).

More preferably though, the HEXIM1-expressing polynucleotide is delivered in a viral vector, wherein the amount of HEXIM1 is increased by introducing in the cell a viral vector that expresses recombinant HEXIM1. The HEXIM1 is expressed from the vector in an amount that is effective to bind to and inactivate enough P-TEFb to result in a decrease in HIV transcription. Vectors used for HEXIM1 gene delivery include lentiviral vectors (Sutton et al., 1998), retroviral vectors (Ranga et al., 1998), and adenoviral vectors (Hamid et al., 2003; Zhou et al., 2000; Gao et al. 2004). For HIV gene therapy, the greatest gene transfer efficiency has been achieved using retroviral or, more recently, lentiviral vectors (Poluri et al. 2003). Infected cellular targets for HIV gene therapy include CD4+ T cells, dendritic cells, macrophages, and their progenitors and stem cells (e.g. hematopoietic stem cells). An exemplary treatment involves the removal of T cells from patients infected with HIV, treating these immune cells with a HEXIM1-expressing lentiviral vector, and then reintroducing the cells back into the patient, as further exemplified in Example 1.

The HEXIM1 expressed by the viral vector may have an N-terminus truncation, and in a specific embodiment, has a 149 amino acid N-terminal truncation. Our data show that deletion of the N-terminal half of HEXIM1 creates a hyperactive transcriptional inhibitor with enhanced targeting/inactivation of P-TEFb. Any number of the first 149 amino acids of HEXIM1 may be deleted without adversely affecting binding of HEXIM1 to 7SK and P-TEFb, whereas amino acids necessary for HEXIM1 to bind to 7SK and P-TEFb should be retained, as should preferably amino acids 150–177, which comprise the nuclear localization signal (NLS) of HEXIM1.

In another embodiment of the invention, the amount of HEXIM1 is increased by introducing in the cell a hybrid polar compound such as hexamethylene bisacetamide (HMBA), or an HMBA derivative. This class compounds has been extensively studied as potent inducers of transformed cell differentiation, and includes in addition to HMBA, suberoylanilide hydroxamic acid (SAHA), m-carboxycinnamic acid bishydroxamide (CBHA), 6-(3-chlorophenylurcido) caproic hydroxamic acid (3-Cl-UCHA), diethyl bis-(pentamethylene-N,N-dimethylcarboxamide) malonate (EMBA), suberic bishydroxamic acid (SBHA), suberoyl-3-aminopyridineamide hydroxamic acid (pyroxamide), hexamethylene bis-(3-pyridin) amide (HMBPA) and ethylenediaminetetra acetic acid cobalt (Co-HDTA). The structure, synthesis, and biological activity of these and other hybrid polar compounds are well-known in the art (Wang et at., 2002; Butler et al., 2001; and Richon et at., 1996 and 1998). These compounds are administered according to well-established methodologies (osmotic pump, intracoronary injection, infusion, etc.). In particular, applicable protocols for administration of HMBA and related compounds are readily derived from the extensive clinical trials of HMBA for the treatment of acute myelogenous leukemia. In one exemplary method, HMBA is administered by continuous infusion as described in Example 2.

In an alternative embodiment, the invention provides methods for decreasing the amount of HEXIM1 by introducing in the cell an amount of HEXIM1 interfering RNA effective to decrease HEXIM1 expression; this method may further comprise contacting the HIV-infected cell with an agent active against replicating HIV virus. The interfering RNA may be introduced in the cell by a viral vector, such as a lentiviral vector. This method has utility in triggering latent virus to undergo replication, and can be used in conjunction with anti-viral drugs that are primarily active against replicating virus (e.g. protease inhibitor drug therapy referred to as "highly active antiretroviral therapy" (HAART)). In one embodiment of the invention, the interfering RNA is introduced in the cell by a viral vector. Lentivirus-based vectors have been used successfully to transduce T cells with siRNA, with up to 10-fold inhibition of expression of the targeted gene (Qin et al., 2003). In a preferred embodiment, the interfering RNA is a small interfering RNA (siRNA) that comprises 18 to 22 nucleotides, and further preferably targets a region with nucleotides 530 to 584 of HEXIM1 mRNA.

After or concurrent with HEXIM1 treatment, a resultant decrease or increase in HIV transcription or replication, as the case may be, is detected. HIV transcription or replication can be quantified inferentially by measuring viral load, which is the major prognostic marker for disease prognosis and outcome of antiretroviral therapy in the treatment of HIV-infected individuals. Applicable methodologies for viral load quantification include: reverse transcriptase-polymerase chain reaction (RT-PCR; Amplicor HIV-1 Monitor Test, Roche Diagnostic Systems, Pleasanton, Calif.), nucleic acid sequence-based amplification (NASBA; NucliSens HIV-1 QT Test, Organon Teknika, Bostel, The Netherlands); and a signal amplification methodology termed branched-chain DNA (bDNA) technique (Quantiplex HIV-1 RNA test, Bayer Diagnostics, Emeryville, Calif.). Because transfection with viral vectors or contacting with inducers of HEXIM1 expression can effect short-term increases in HIV transcription, the subject methods for inhibiting HIV replication typically defer detecting the required resultant decrease in HIV replication for a time after the increasing step sufficient to allow elevated expression and resultant measurable action of the HEXIM1 through P-TEFb inhibition. This time period necessarily depends on how the HIV replication is measured, but is typically at least 24 hr, preferably at least 48 hrs, more preferably at least 72 hrs.

Another aspect of the invention is a method for inhibiting cardiac hypertrophy in a patient, the method comprising the steps of determining that the patient has, or is susceptible to, cardiac hypertrophy, increasing the amount of active HEXIM1 in the patient's cardiomyocytes; and detecting a resultant inhibition in cardiac hypertrophy. Clinical analysis and diagnostic methods currently used in the evaluation of heart diseases and disorders are used to determine whether a patient has or is susceptible to cardiac hypertrophy. Cardiac hypertrophy often occurs after myocardial infarction. Various types of heart disease are also associated with hypertrophic conditions, most notably hypertensive cardiomyopathy and hypertrophic cardiomyopathy (HC). Hypertensive cardiomyopathy often presents with left ventricular hypertrophy in association with features of dilated cardiomyopathy or restrictive cardiomyopathy with cardiac failure. HC, which is more prevalent, is characterized by a thickening of abnormal heart tissue which can result in shortness of breath, progressive heart failure, and sudden death. The majority of HC cases are believed to result form genetic defects. It is estimated that one in 500 people carry an altered gene that can cause HC. Mutations in a number of genes have been identified. Familial hypertrophic cardiomyopathy is caused by a mutation in one of nine genes that encode sarcomere proteins. A tenth gene has been identified that is a non-sarcomere protein (a subunit of protein kinase A) is associated with individuals who have both hypertrophic cardiomyopathy and Wolf-Parkinson-White syndrome (Charron, et al., 2003).

In a patient selected for treatment, the amount of HEXIM1 in the patient's cardiomyocytes is caused to be increased to a level sufficient to bind enough P-TEFb to inactivate it and result in a decrease in transcription, thereby reducing the size of hypertrophic cardiomyocytes and/or the degree of hypertrophy. The HEXIM1 may have an N-terminus truncation, and in a specific embodiment, has a 149 amino acid N-terminal truncation, as described above. In one embodiment of the invention, the amount of HEXIM1 is increased by introducing in the patient's cardiomyocytes a viral vector that expresses recombinant HEXIM1. Adenoviral vectors have been widely used for gene transfer to cardiomyocytes (Chaudrhi et al., 2004; Williams et al., 2004; Wang et al., 2003; Li et al., 2003; and Gao et al., 2004). In an exemplary procedure, the viral vector is introduced into a patient with, or susceptible to, cardiac hypertrophy by intracoronary injection (Gao et al., 2004). Methods for making adenoviral constructs suitable for intracoronary injection for the treatment of heart disease are known in the art, e.g. as detailed by Hammond et al. (U.S. Pat. No. 6,174,871). Adenoviral delivery of HEXIM1 is exemplified further in Example 4.

In another embodiment of the invention, the amount of HEXIM1 is increased by introducing in the cell a hybrid polar compound such as hexamethylene bisacetamide (HMBA), or an HMBA derivative, as described above. In one exemplary method, HMBA is administered by continuous infusion as exemplified in Example 3.

The subject methods for inhibiting cardiac hypertrophy typically defer detecting the resultant decrease in cardiac hypertrophy for a time after the increasing step sufficient to allow elevated expression and resultant measurable action of the HEXIM1 through P-TEFb inhibition. This time period necessarily depends on how the cardiac hypertrophy is measured, but is typically at least 24 hr, preferably at least 48 hrs, more preferably at least 72 hrs. Cardiac hypertrophy is detected by conventional clinical analysis and diagnostic methods (supra).

Another aspect of the invention is a method of screening for an agent that modulates HEXIM1-P-TEFb binding, the method comprising the steps of incubating a mixture of reconstituted 7SK RNA, P-TEFb, and HEXIM1, with a candidate modulating agent under conditions wherein but for the presence of the agent, the 7SK RNA, P-TEFb, and HEXIM1 engage in a reference binding; and detecting an agent-biased binding of the HEXIM1 to the P-TEFb, wherein a difference between the reference binding and the agent-biased binding indicates that the agent modulates HEXIM1-P-TEFb binding. A mixture of reconstituted 7SK RNA, P-TEFb, and HEXIM1 has quantifiable or controllable amounts of 7SK RNA and/or HEXIM1 such that one or the other of these components can be excluded from the mixture to prevent HEXIM1 binding to, and resultant activation of, P-TEFb. In preferred embodiments each of these components is essentially purified from other cellular components prior to inclusion in the mixture, and constitutes preferably at least 90%, 95%, or 99% of a protein fraction. Affinity purification methods can be used.

Candidate modulating agents are added to the reconstituted mixture, and agent-biased binding of the HEXIM1 to the P-TEFb is detected relative to reference binding, which is the measure of binding that would otherwise occur in the absence of the added agent. The candidate modulating agents can be agents that are being developed and/or evaluated for therapeutic use, e.g. for treatment of HIV infection, cardiac hypertrophy, hyperproliferative disorders and diseases such as cancer, etc. Examples of candidate modulating agents include small molecules (i.e. molecular weight of less than 1000 kilodaltons), peptide therapeutics, and antisense nucleic acids. The binding of HEXIM1 with P-TEFb can be detected directly, for example in a coprecipitation binding assay or in a solid-phase binding assay. Binding can also be detected indirectly for example, in a transcriptional readout assay, a viral replication assay, or in a kinase assay. Kinase assays can be performed in multi-well microtiter plates, and thus are amenable to high-throughput screening for the identification of modulating agents in a compound library. Exemplary assays are described in Example 5. Modulating agents identified in the binding assay can be utilized in structure-activity-relationship analyses and/or animal models to further document specific therapeutic applications.

Another aspect of the invention is a method of screening for an agent that inhibits pathogenesis associated with HEXIM1 underexpression, the method comprising the steps of contacting a pathogenically HEXIM1 underexpressing cell with an HEXIM1 upregulator, and detecting a resultant inhibition of the pathogenesis. In one embodiment, the inhibition is inhibition of HIV replication in an HIV-infected cell. In another embodiment, the pathogenesis is cardiac hypertrophy.

Agents that upregulate HEXIM1 can be identified by contacting a cell capable of HEXIM1 expression with a candidate agent, and measuring increased HEXIM1 mRNA and/or protein expression. Cells that endogenously express HEXIM1, such as cultured smooth muscle cells (Ouchida et al., 2003) or breast epithelial cells (Wittmann et al., 2003) can be used to test for agent-induced increased HEXIM1 expression. The agent is administered to the cell and methods known in the art are used to measure HEXIM1 expression. Methods for measuring mRNA expression include Northern blotting, slot blotting, ribonuclease protection, quantitative RT-PCR (e.g., using the TaqMan.RTM., PE Applied Biosystems), or microarray analysis. Optionally, protein expression can be measured using various methods known in the art including Western blotting, ELISA, or in situ detection.

Agents that increase HEXIM1 expression can be tested for their ability to inhibit HIV replication in an HIV-infected cell in vitro or in vivo. A variety of assays for measuring HIV replication in a cell are known in the art. In one exemplary assay, human brain tissue aggregates infected with HIV-1 SF 162 are cultured for 4 weeks and exposed to agents identified as increasing HEXIM1 expression. The agent is added to the aggregates either 24 hours prior to, simultaneously with, or 24 hours post infection. Viral replication is assessed by p24 enzyme-linked immunosorbent assay (ELISA) in culture medium (Kandanearatchi et al., 2004).

Agents can be tested for inhibiting cardiac hypertrophy by contacting the agent with a cardiomyocyte that is hypertrophic or susceptible to hypertrophy, and detecting a resultant inhibition of cardiomyocyte hypertrophy. Assays are known in the art for measuring the effects of test agents on cardiac myocytes. In an exemplary assay, the effect of agents identified as increasing HEXIM1 expression are tested on hypertrophied atria from monocrotaline-treated rats using previously described methods (Han et al., 2004).

EXAMPLES

Example 1

HEXIM1 Treatment for HIV-infection

Methods adapted from Qin et al. (2003) are used to construct lentiviral vectors expressing recombinant HEXIM1, transduce human T cells in vitro with HEXIM1-expressing lentiviral vector, and to show reduction of HIV-1 replication in transduced T cells. Briefly, a human U6-RNA pol III promoter promoter (−328 to +1) is amplified from HEK-293 genomic DNA with appropriately selected primers in which a BbsI site is introduced at the 3' end allowing insertion of the HEXIM1 sequence at the +1 position of the U6 transcript. The PCR fragment is cloned at EcoRI-HindIII sites of pBS-SKII plasmid (Stratagene). Transient transfection assays show that the promoter fragment is fully functional.

The lentiviral vector is derived from FUGW (Lois et al., Science (2002) 295:868–872). The extra nucleotides from the HindIII site downstream of the Ubiquitin-C promoter (UbiC) to the NcoI site in front of the initiation codon of GFP are deleted by a HindIII-NcoI adapter ligation. Further, XbaI, EcoRI, and XhoI sites at the 3' end of GFP and WRE are eliminated, followed by a polylinker oligonucleotide ligation at the PacI site between the Flap element and the UbiC promoter, to generate a set of new restriction sites, XbaI-HpaI-XhoI-BstXI-PacI. To construct the HEXIM1-expressing lentiviral vectors, the HEXIM1 expression cassette is subcloned into the vector between the XbaI and XhoI sites. The resulting plasmid is confirmed by restriction enzyme digestion and DNA sequencing.

Vesicular stomatitis virus (VSV)-G pseudotyped lentiviral vector stocks are produced by calcium phosphate-mediated transient transfection of HEK-293 T cells. The T cells are cultured in DMEM containing 10% FCS, 100 units of penicillin, and 100 µg/ml streptomycin. The cells are cotransfected with appropriate amounts of vector plasmid, the HIV-1 lentiviral packaging constructs pRSVREV and pMDLg/pRRE (Dull et al., J. Virol. (1998) 72:8463–8471), and the VSV-G expression plasmid pHCMVG (Yee et al., Methods Cell Biol (1994) 43:99–112). The viruses are collected from the culture supernatants on days 2 and 3 post-transfection and concentrated 100- to 1,000-fold by ultracentrifugation. The concentrated virus stocks are tittered on HEK-293 T cells based on GFP expression.

Magi-CCR5 cells (NIH AIDS Research and Reference Reagent Program) are maintained in DMEM, 10% FCS containing 200 μg/ml puromycin (Sigma). The cells are transduced with concentrated lentiviral vector stocks at a multiplicity of infection (moi) of 10–25 in the presence of 8 μg/ml polybrene (Sigma). The transduced cells are harvested 4 days later and stained with cy-chrome-labeled mouse anti-human CCR5 mAb (2D7, PharMingen) according to manufacturer instructions. Human peripheral blood lymphocytes (PBLs) are isolated from leukopacks by Histopaque (Sigma) and cultured in RPMI medium 1640/20% FCS with 2.5 μg of phytohemagglutinin (PHA) (Murex Biotech, Dartford, U.K.)/100 units of penicillin/100 μg/ml streptomycin for 2 days. After 2 days of PHA stimulation, CD8+ cells are depleted by M450 CD8 Dynabeads (Dynal, Great neck, N.Y.) and the residual amount of CD8+ cells is <1%, as confirmed by FACS analysis. The CD8+-depleted PBLs are used for lentiviral vector transduction. Briefly, $4 \times 10^5$ cells are incubated with lentiviral vector at a moi of 5 for 2 h in the presence of 8 μg/ml polybrene. After the incubation, virus supernatants are removed and replaced with 1.5 ml of fresh RPMI medium 1640/20% FCS containing 20 units/ml IL-2 (Roche Molecular biochemicals).

Stocks for the murine heat-stable antigen (HAS)-expressing HIV-1 reporter virus, NFNSX-r-HSAS (CCR5-tropic; Steinberger et al., Proc. Natl. Acad Sci. USA (2000) 97:805–810) are produced by calcium phosphate transfection with the infectious proviral plasmid in HEK-293 T cells. The virus supernatants are filtered with 0.22-μm filters. Four days after lentivector transduction, the PBLs ($5 \times 10^5$ cells) are infected with 100 μl of NFNSX-r-HSAS virus in the presence of 8 μg/ml polybrene for 2 h. After incubation, the cells are washed and replated with 1.5 ml of RPMI medium 1640/20% FCS and 20 units/ml IL-2. The rate of infection is determined by FACS analysis for HAS expression on the cell surface at various time points. P24 levels in the culture supernatants are measured by ELISA.

For measuring HIV-1 reporter virus infection, a PE-labeled antimurine HAS mAb (M1/69, PharMingen) is used. The cells are also stained with isotype controls for each of the specific antibodies. The stained cells are fixed with 2% formaldehyde and acquired on a FACScan or FACSCalibur (Becton Dickinson). Data analysis is performed with CELLQUEST (Becton Dickinson) or FLOWJO (Tree Star, San Carlos, Calif.) software. Expression of recombinant HEXIM1 in lymphocytes correlates with inhibition of HIV-1 infection after 48 hours, and for at least 8 days. The recombinant HEXIM1 results in an overall reduction of virus load.

Methodology adapted from NIH gene transfer protocol no. 0107-488 (VRX496) is used to treat HIV-infected patients with HEXIM1-expressing lentiviral vector. Patients meet the following criteria: not responsive to anti-retroviral drug therapy regimens, no opportunistic infections, CD4 count of 200–500, and viral load >5,000. Peripheral blood mononuclear cells (PBMCs) are isolated from patients by Ficoll-hypaque density gradient separation. Blood is collected in CPT tubes (Becton-Dickinson, Franklin Lakes, N.J., USA), and the cells are isolated by centrifugation at 2600 rpm for 30 minutes at room temperature, then plasma is removed and cells are resuspended in blocking buffer. CD4+ T lymphocytes are subsequently purified to >95% by positive selection by MACS (Miltenyi Biotec, Auburn, Calif., USA). Purity is determined by flow cytometry. The purified T lymphocytes are mixed with lentiviral vector expressing recombinant HEXIM1 (described above) and cultured in X-Vivo-15 (BioWhittaker) and expanded 8–11 days ex vivo using methods adapted from Humeau et al. (2004). Each patient receives an intravenous injection of $1 \times 10^{10}$ cells infused over 30 minutes. Patients are examined 24, 48, and 72 hours post-injection and weekly for 4 weeks. Follow-up examinations are conducted 1, 3, and 6 months post-injection to measure reduction in viral load, where determinations are made whether to administer additional doses. Patients are monitored in long-term follow-up for reduction in viral load and for testing of replication competent lentivirus.

Example 2

HMBA Treatment for HIV Infection

Methodology adapted from Lin et al. (Proc Natl Acad Sci U S A. (2003) 100(19):11013–8) demonstrates inhibition of HIV replication in HIV-infected cells treated with hybrid polar compounds (HPCs). Cell lines (MT-2, MT-4, PM1, HeLa-CD4, and U87-CD4), HIV-1 laboratory strains (LAI, HXB2, JRFL, Ba-L, MN, IIIB, AO-18, SF-2, and SF-162), and clinical isolates are obtained from the National Institutes of Health AIDS Reagent Repository; HIV-1$_{89.6}$ is obtained from Advanced Biotechnologies (Columbia, Md.); and HepG2, human foreskin fibroblast, U373-MG, SK-N-MC, SK-N-SH, HT-29, 293, and Huh-7 cells are obtained from the American Type Culture Collection.

Cytotoxicity assays are performed in the presence of serially diluted HPCs for 6 days, and cell viability is quantitated by using an XTT assay (hill et al., J. Virol. (1997) 71:6296–6304) to assess HepG2, Huh-7, 293, human foreskin fibroblast, HeLa-CD4, U373-MG, SK-N-MC, SK-N-SH, HT-29, PMI, MT-2, MT-4, macrophages, and peripheral blood mononuclear cells (PBMCs).

Experiments are done using a single-cycle viral infection assay (Donzella et al., Nat. Med. (1998) 4:72–77). HIV-1 with a luciferase reporter gene and pseudotyped with an HIV-1JRFL envelope is used to infect HeLa CD4+ CCR5+ cells in the presence of varying concentrations of HPCs. The compounds are applied at various times after infection. Antiviral activity is determined by quantitating luciferase activity (Promega). Increases in HEXIM1 expression are measured by RT-PCR at 48, 60, and 72 hours after HPC administration and are determined to correlate with a resultant reduction in viral load.

Studies are conducted in rats, dogs, and cynomolgus monkeys after i.v. administration of HPCs in a solution formulation (90% polyethylene glycol 400/10% ethanol). The i.v. doses are 1 mg/kg in rats and 0.67 mg/kg in dogs and monkeys. Animals are fasted overnight, and plasma samples are collected before and after dosing for 24 h (8 h in rats). The drug concentrations in plasma are determined by liquid chromatography tandem mass spectrometry (LC/MS/MS) after protein precipitation of samples. The pharmacokinetic parameters (area under the curve, bioavailability, clearance, and half-life, etc.) are calculated from the plasma concentration time data by noncompartmental analysis using KINETICA software (version 3.0, InnaPhase, Philadelphia).

Methodology adapted from Andreeff et al. (1992) is used to treat HIV-infected patients with hexamethylene bisacetamide (HMBA). Patients meet the following criteria: not responsive to anti-retroviral drug therapy regimens, no opportunistic infections, CD4 count of 200–500, and viral load >5,000. A 5% solution of HMBA (NSC-95580) in distilled water is provided in 500-ml infusion bottles (25 g total per bottle). HMBA is administered at a dose of 24 g/m²/d in 10-day courses, followed by an 18- to 75-day observation period. Plasma levels are determined daily (at 24 hours into the infusion). HMBA dosage is adjusted to achieve a steady-state HMBA plasma level of 1.2±0.15 mmol/L. Dosages are reduced by 25% in patients experiencing grade III toxicity (in accordance with WHO criteria). HMBA plasma levels are determined using HPLC. In patients showing a reduction in viral load, treatment is repeated at approximately 4-week intervals, unless limiting toxicities ensue. HMBA plasma levels are maintained at 0.75 to 1.0 mmol/L. Follow-up examinations are conducted 1, 3, and 6 months post-treatment to measure reduction in viral load and to determine whether to administer additional doses of HMBA.

Example 3

HMBA Treatment for Cardiomyocyte Hypertrophy

In a method adapted from Perrier et al. (2004), myocardial infarction (MI) is induced in 250 to 280 g male Wistar rats by left coronary artery ligation. Only post-MI hearts that show a transmural scar are used. An osmotic minipump (Alzet 2ML4) is implanted subcutaneously at the time of surgery to deliver varying amounts of HMBA or other HPC. Control animals receive carrier solution only. Cellular responses are examined over time using whole-cell, patch-clamp techniques on right ventricular myocytes. Animals are euthanized 1 and 3 weeks after surgery with intraperitoneal injection of sodium pentobarbital. Ventricular myocytes are isolated enzymatically. Cellular hypertrophy is monitored by 2-photon microscopy (Zeiss LSM 510 NLO) to calculate cell volume and the whole-cell patch-clamp technique is used to measure membrane capacitance, an electrical index of membrane surface area. To measure cell volume, the voltage-sensitive dye 1-(3-sulfonatopropyl)-8-[b-[2-(di-n-butylamino)-6-naphthyl]vinyl]pyridium betaine (di-4-ANEPPS)-loaded cells are illuminated at 840 nm with a mode-locked Ti:sapphire laser (Mira 900, Coherent) and recorded in 3D. Images of spherical beads (Molecular Probes) are recorded under the same conditions to calculate the point spread function. Deconvolution is performed with Huygens (Bitplane AG). Cell volume is estimated by the myocyte cross-sectional area at the center multiplied by the deconvoluted image thickness. Action potential (AP) and whole-cell current are monitored at 0.1 Hz with an Axopatch 1D amplifier and recorded with pCLAMP-7 (Axon Instruments) at 23° C. to 25° C. Series resistance is electronically compensated (40% to 60%). AP and $K^+$ are measured. One week after myocardial infarction, no sign of cellular hypertrophy is found, but action potential duration is lengthened in control animals. Three weeks after myocardial infarction, prolongation of action potential endured in control animals and cellular hypertrophy develops. HMBA-treated animals have normal action potential and show no signs of cellular hypertrophy.

Genetic testing, and/or ECG and echocardiography are used to diagnose patients susceptible to hypertrophic cardiomyopathy using methods described by Charron et al. (1997 & 2003). For genetic testing, candidate patients are from families involved in genetic studies in whom genetic analyses are performed and the causative mutation identified. Patients are identified as being at risk of inheriting the disease gene, i.e., they have a first-degree relative clinically affected by hypertrophic cardiomyopathy. The major diagnostic criteria for echocardiography are a left ventricular wall thickness >13 mm and, for ECG, abnormal Q waves, left ventricular hypertrophy, and marked ST-T changes. Clinical evaluation is performed, and blood samples are obtained. Using methods adapted from Andreeff et al. (1992), patients diagnosed as having or susceptible to cardiac hypertrophy are given HMBA treatment. A 5% solution of HMBA (NSC-95580) in distilled water is provided in 500-ml infusion bottles (25 g total per bottle). HMBA is administered at a dose of 24 g/m²/d in 10-day courses, followed by an 18- to 75-day observation period. Plasma levels are determined daily (at 24 hours into the infusion). HMBA dosage is adjusted to achieve a steady-state HMBA plasma level of 1.2±0.15 mmol/L. Dosages are reduced by 25% in patients experiencing grade III toxicity (in accordance with WHO criteria). HMBA plasma levels are determined using HPLC. In certain patients, morphologic analyses provide evidence that HMBA treatment reduces cardiac hypertrophy. The most prominent toxicity is thrombocytopenia, generally reversible on cessation of administration of HMBA.

Example 4

HEXIM1 Treatment for Cardiac Hypertophy

Methodology adapted from Rosengart et al. (Circulation (1999) 100:468–474) is used to construct an adenovirus gene-transfer vector for expression of recombinant HEXIM1. The vector is based on the genome of the Ad5 serotype, with deletions in the E1 and E3 regions. The expression cassette is in the E1 region and contains (right to left) the cytomegalovirus early/immediate enhancer/promoter, an artificial splice sequence, human HEXIM cDNA, and the SV40 polyA/stop signal. The viral vector is propagated in 293 cells, purified by CsCl density gradients, dialyzed, and stored at −70° C. The vector meets all safety criteria established by the Food and Drug Administration Bureau of Biologics (FDA BB) for clinical grade Ad vector preparations (FDA BB-IND 7381), including no detectable endotoxin or infectious agents and ≦1 replication-competent Ad for the total dose to be delivered. The vector is titered in plaque-forming units (pfu) and characterized as to particle units (pu) with the absorbance at 260 nm and the extinction coefficient for Ad ($9.09 \times 10^{-12}$ mL·particles⁻¹·cm⁻¹). Just before use, the vector is thawed, diluted in a 3% sucrose solution, drawn up as 100 □L in 1-mL-insulin syringes with a 27-gauge needle (Becton Dickinson).

MI is induced in 250 to 280 g male Wistar rats by left coronary artery ligation as described above. The HEXIM1/ adenoviral vector is administered by direct myocardial injection to an affected region. Control animals receive vector lacking the HEXIM1 coding region. Cellular responses are examined over time using whole-cell, patch-clamp techniques on right ventricular myocytes. Animals are euthanized 1 and 3 weeks after surgery with intraperitoneal injection of sodium pentobarbital. Ventricular myocytes are isolated enzymatically. Cellular hypertrophy is monitored by 2-photon microscopy (Zeiss LSM 510 NLO) to calculate cell volume and the whole-cell patch-clamp technique is used to measure membrane capacitance, an electrical index of membrane surface area. To measure cell volume, the voltage-sensitive dye 1-(3-sulfonatopropyl)-8-[b-[2-(di-n-butylamino)-6-naphthyl]vinyl]pyridium betaine (di-4-ANEPPS)-loaded cells are illuminated at 840 nm with a mode-locked Ti:sapphire laser (Mira 900, Coherent) and recorded in 3D. Images of spherical beads (Molecular Probes) are recorded. under the same conditions to calculate the point spread function. Deconvolution is performed with Huygens (Bitplane AG). Cell volume is estimated by the myocyte cross-sectional area at the center multiplied by the deconvoluted image thickness. Action potential (AP) and whole-cell current are monitored at 0.1 Hz with an Axopatch 1 D amplifier and recorded with pCLAMP-7 (Axon Instruments) at 23° C. to 25° C. Series resistance is electronically compensated (40% to 60%). AP and K$^+$ are measured. One week after myocardial infarction, no sign of cellular hypertrophy is found, but action potential duration is lengthened in control animals. Three weeks after myocardial infarction, prolongation of action potential endured in control animals and cellular hypertrophy develops. HMBA-treated animals have normal action potential and show no signs of cellular hypertrophy.

Genetic testing and ECG and echocardiography are used to diagnose patients susceptible to hypertrophic cardiomyopathy using methods described above. The vector is administered by direct myocardial injection to a region of cardiac hypertrophy at a dose of 4×10$^9$ pu/patient. Morphological analysis and stress testing indicate resultant decrease in cardiac hypertrophy.

Example 5

Assays for HEXIM1-Modulating Agents

7SK snRNP is reconstituted in vitro for use in kinase assays to identify modulating agents. 250 □g of nuclear extract (NE) prepared from either F1C2 (a Heta-based cell line expressing CDK9-Flag) (Yang et al., 2001) or HeLa cells (a negative control) is incubated at 4° C. for 2 hr with 10□of anti-Flag beads (Sigma). The beads are then washed with a buffer containing 0.3 M KCl (D0.3M) and then D0.8M to strip 7SK and HEXIM1 off P-TEFb. The immobilized 7SK/HEXIM1(–) P-TEFb is washed with D0.1M. Beads are blocked for 30 min with 20□of a blocking solution containing 5 mg/ml BSA, 3 mg/ml poly(C), and 2.5 mg/ml E. coli tRNA and then incubated at 30° C. for 30 min in D0.1M plus 0.5 mM ATP, 5 mM MgCl$_2$ and 100 □g of HeLa NE. After incubation, the beads are washed with D0.4M and then D0.1M. The reconstituted 7SK snRNP is eluted off the beads with 0.4 mg/ml of Flag peptide prepared in D0.1M. Both 7SK and HEXIM1 associated with the P-TEFb-beads isolated from F1C2 NE containing CDK9-Flag.

In binding assays, reconstituted 7SK RNA, P-TEFb, and HEXIM1 are incubated under conditions that, but for the presence of a test agent, allow both 7SK and HEXIM1 to associate with P-TEFb and provide a reference binding of HEXIM1 and P-TEFb (i.e. control). Test agents are added during the incubation step, and agent-biased binding is detected to identify agents that modulates HEXIM1-P-TEFb binding.

In kinase assays, reconstituted 7SK RNA, P-TEFb, HEXIM1 are incubated under conditions that, but for the presence of a test agent, allow both 7SK and HEXIM1 to associate with P-TEFb to provide a reference kinase activity. Kinase reactions amenable to high throughput screening are performed at 30° C. for 25 min, and contain 5 mM MgCl$_2$, 50 μM cold ATP, 1 μl γ[P$^{32}$]-ATP (3000 Ci/mmol), 1 μg immobilized GST-CTD, and an amount of 7SK snRNP determined empirically. Test agents that result in an increase or decrease in kinase activity relative to control are identified as agents that modulate HEXIM1-P-TEFb binding.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

Andreeff et al., Blood. (1992) 80:2604–2609
Butler et al., Clin Cancer Res. (2001) 7:962–970
Charron et al., Circulation (1997) 96:214–219
Charron et al., Arch Mal Coeur Vaiss. (2003) 96:1042–1047
Gao et al., Hum Gene Ther. (2004) 15:574–587
Ghatpande et al., Dev. Biol. (1999) 208:210–221
Hamid et al., J. Clin. Oncol. (2003) 21:1489–1504
Han et al., Hypertension (2004) 43:243–248
Huang et al., Gene (2002) 292:245–259
Humeau et al., Mol Ther. (2004) 9:902–913
Kandanearatchi et al., J Neurovirol. (2004) 10:136–139
Li et al., Gene Ther. (2003) 10:1807–1813
Michels et al., Mol. Cell. Biol. (2003) 23:4859–4869
Ouchida et al., Genes Cells (2003) 8:95–107
Perrier et al., Circulation (2004) August 2 [Epub ahead of print; PMID: 15289366]
Poluri et al., Expert Opin Biol. Ther. (2003) 3:951–963
Qin et al., PNAS (2003) 100:183–188
Ranga et al., Proc. Natl. Acad. Sci. USA (1998) 95:1201–1206
Richon et al., Proc Natl Acad Sci U S A. (1998) 95:3003–3007
Richon et al., Proc Natl Acad Sci U S A. (1996) 93:5705–5708
Sano et al., Nat. Med. (2002) 8:1310–1317
Sutton et al., J. Virol. (1998) 72:5781–5788
Wang et al., Chin Med Sci J. (2002) 17:27–31
Wittmann et al., Cancer Res. (2003) 63:5151–5158
Williams et al., Circulation (2004) 109:1590–1593
Yang et al., Nature (2001) 414:317–322
Zhou et al., Virology (2000) 275:348–357

What is claimed is:

1. A method for inhibiting HIV replication in a patient, the method comprising the steps of:
    determining that the patient is HIV-infected and a target for HEXIM1 therapy;
    increasing the amount of active HEXIM1 in HIV-infected cells of the patient; and
    detecting a resultant decrease in HIV replication at least 48 hr after the increasing step, wherein the amount of HEXIM1 is increased by introducing in the cell an agent that is a hybrid polar compound selected from the group consisting of: hexamethylene bisacetamide (HMBA) and hexamethylene bis-(3-pyridin)amide (HMBPA).

2. The method of claim 1 wherein the agent is hexamethylene bisacetamide (HMBA).

3. The method of claim 1 wherein the agent is hexamethylene bis-(3-pyridin)amide (HMBPA).

4. The method of claim 1 wherein the agent is introduced by infusion in the patient, and the resultant decrease in HIV replication is detected at least 72 hr after the increasing step.

5. The method of claim 2 wherein the agent is introduced by infusion in the patient, and the resultant decrease in HIV replication is detected at least 72 hr after the increasing step.

6. The method of claim 3 wherein the agent is introduced by infusion in the patient, and the resultant decrease in HIV replication is detected at least 72 hr after the increasing step.

* * * * *